US008123541B2

(12) United States Patent
Hsu et al.

(10) Patent No.: US 8,123,541 B2
(45) Date of Patent: Feb. 28, 2012

(54) ELECTRICAL CONNECTOR WITH EXPANDED COVER

(75) Inventors: Shuo-Hsiu Hsu, Tu-Cheng (TW); Hao-Yun Ma, Tu-Cheng (TW); Fang-Jwu Liao, Tu-Cheng (TW)

(73) Assignee: Hon Hai Precision Ind. Co., Ltd., New Taipei (TW)

(*) Notice: Subject to any disclaimer, the term of this patent is extended or adjusted under 35 U.S.C. 154(b) by 0 days.

(21) Appl. No.: 12/773,023

(22) Filed: May 4, 2010

(65) Prior Publication Data

US 2010/0279533 A1 Nov. 4, 2010

(51) Int. Cl.
*H01R 13/62* (2006.01)

(52) U.S. Cl. ........................................................ 439/325

(58) Field of Classification Search .................. 439/626, 439/325, 326, 331, 329; 235/441, 260, 492
See application file for complete search history.

(56) References Cited

U.S. PATENT DOCUMENTS

| | | | | |
|---|---|---|---|---|
| 6,062,889 | A * | 5/2000 | Hyland et al. | 439/326 |
| 2008/0305669 | A1* | 12/2008 | Hong et al. | 439/329 |

* cited by examiner

*Primary Examiner* — Alexander Gilman
(74) *Attorney, Agent, or Firm* — Andrew C. Cheng; Wei Te Chung; Ming Chieh Chang

(57) ABSTRACT

An electrical connector for electrically connecting a module to a printed circuit board, comprises an insulative housing receiving the module, a plurality of contacts received in the insulative housing and a cover pivotally assembled to the insulative housing. The cover presses upon the module and extends beyond a rear end of the insulative housing to further limit or press a part of the module exposed outside the insulative housing. The electrical connector can reliably retain the module.

20 Claims, 3 Drawing Sheets

ELECTRICAL CONNECTOR WITH EXPANDED COVER

BACKGROUND OF THE INVENTION

1. Field of the Invention

The present invention relates to an electrical connector, and more particularly, to an electrical connector with an expanded cover to cover an accessorial module.

2. Description of the Prior Art

Connectors are used in electrically connecting a flexible printed circuit (FPC) with a printed circuit board (PCB). The connector usually comprises a socket body having a number of terminals received therein and a metallic cover assembled to the socket body. The socket body comprises a bottom wall and three sidewalls extending upwardly from the bottom wall. The bottom wall and the sidewalls define a space for disposing a flexible printed circuit (FPC) therein. The cover defines two opposited slots, and side surfaces of the side walls are provided with two pinshafts received in the slots, so that the cover is pivotally assembled to the socket body.

The is FPC received in the insulative housing, sometimes, an accessorial module needs to be mount under the FPC, but the connector only clamps an edge of the FPC by a clamping force of the terminal thereof, the FPC and the accessorial module may swing or deflect when placing the connector upside down or shocking the connector.

In view of the above, an improved electrical connector is needed to overcome the above-mentioned disadvantages.

SUMMARY OF THE INVENTION

Accordingly, an object of the present invention is to provide an electrical connector having expanded cover to reliably clamp a module.

To fulfill the above-mentioned object, An electrical connector, for converting electric and optical signal from a module to a printed circuit board, comprises: an insulative housing comprising plurality of passageways and receiving the module, a plurality of contacts received in the insulative housing; and a cover being pivotally assembled on a front end of the insulative housing and pressing upon the module, the module formed with a rear edge extending beyond a rear end of the insulative housing.

Other objects, advantages and novel features of the invention will become more apparent from the following detailed description when taken in conjunction with the accompanying drawings.

DETAILED DESCRIPTION OF THE PREFERRED EMBODIMENT OF THE INVENTION

Reference will now be made to the drawings to describe the present invention in detail.

Figure 1:
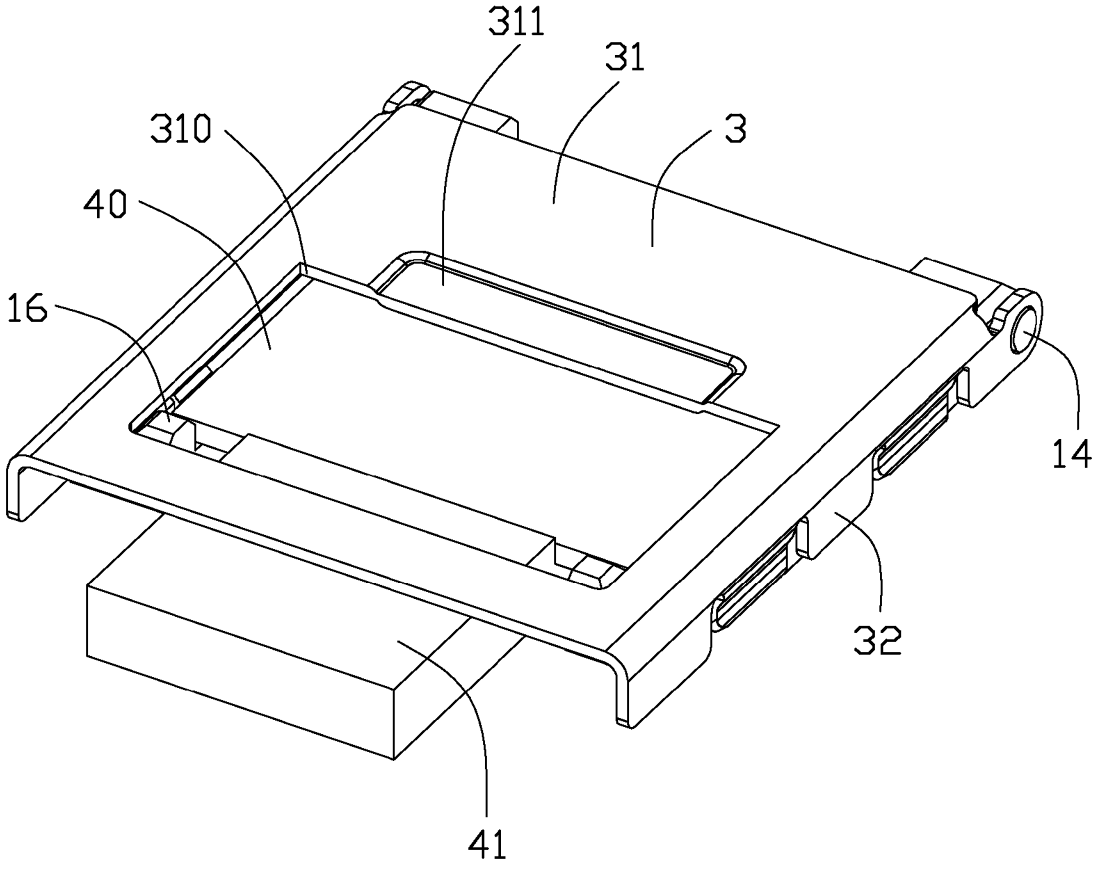
FIG. 1 is an assembled, perspective view of an electrical connector in accordance with a preferred embodiment of the present invention and a module received in the electrical connector, wherein a cover of the electrical connector is in a closed position.
Figure 2:
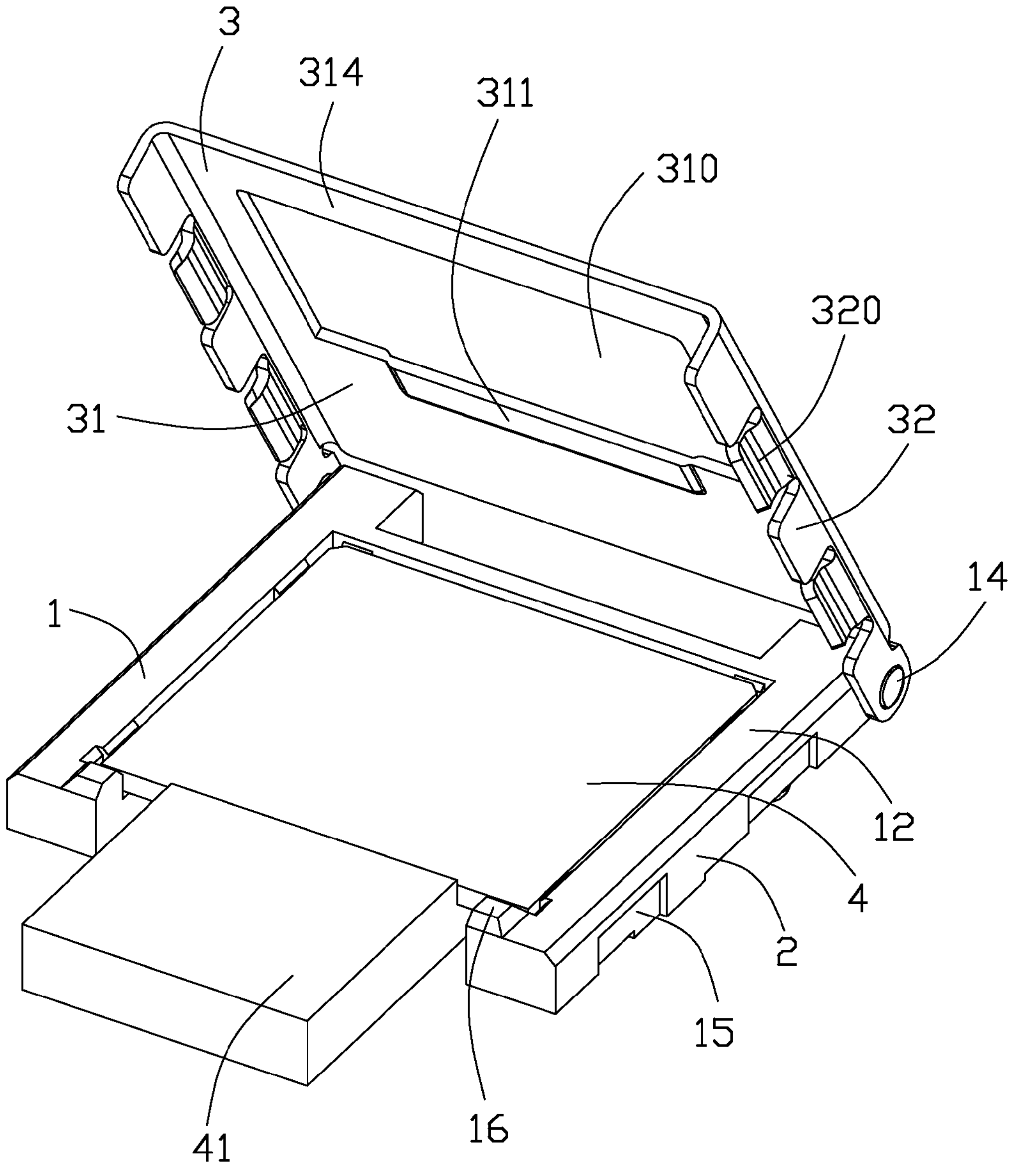
FIG. 2 is similar to FIG. 1, but the cover is in an opened position.
Figure 3:
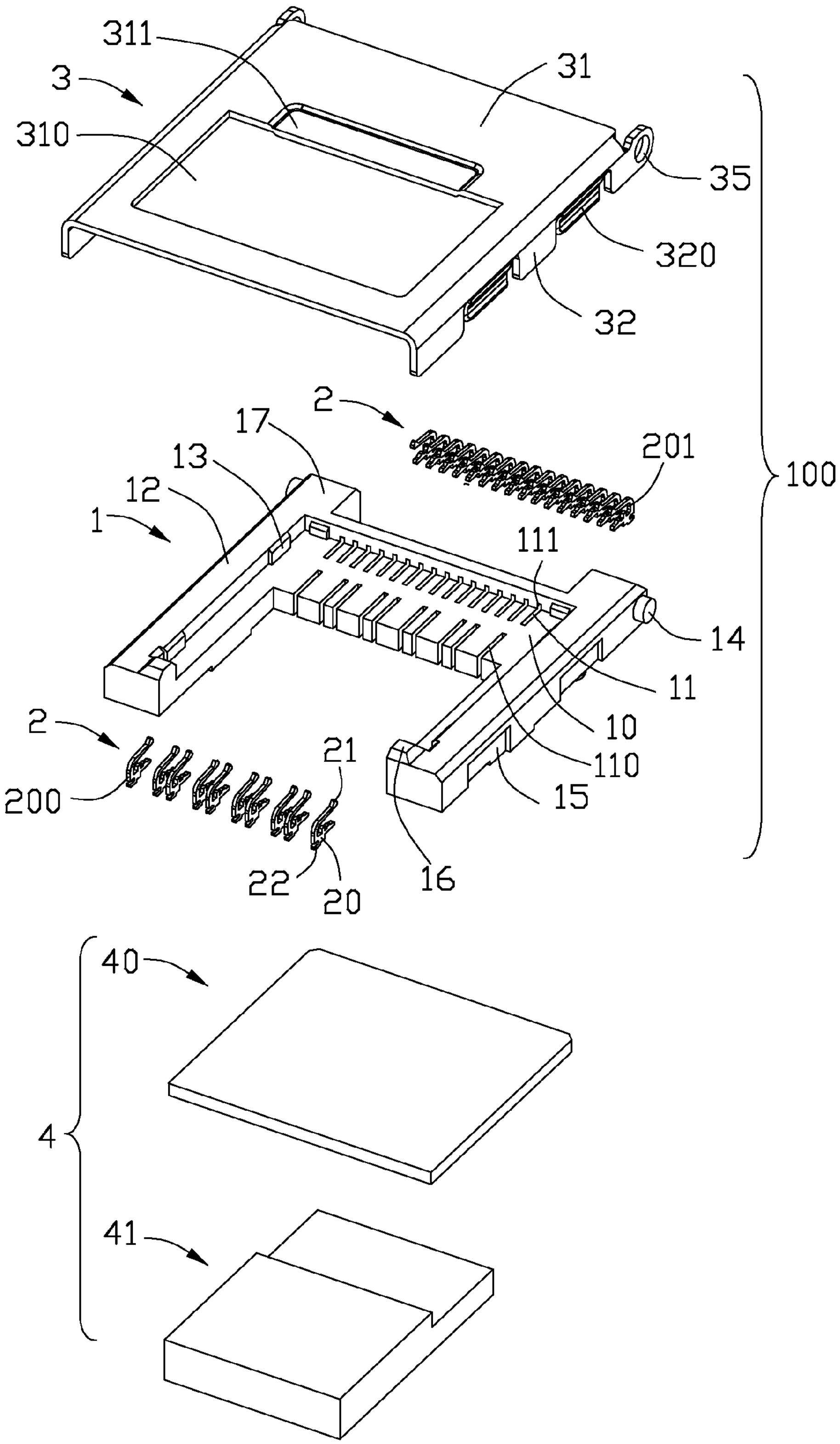
FIG. 3 is an exploded perspective view of the electrical connector.

Referring to FIGS. 1-3, an electrical connector 100 in accordance with the present invention is used to convert electric and optical signal from a module 4 to a circuit substrate (not shown). The electrical connector 100 comprises an insulative housing 1, a plurality of contacts 2 received in the insulative housing 1 and a cover 3 assembled on the insulative housing 1.

The insulative housing 1 substantially has a reverse U shape configuration, and comprises a base 10 defining an opening on a side thereof, and three sidewalls 12 extending upwardly from another three sides of the base 10. The base 10 defines a plurality of passageways 11 including a row of first passageways 110 and a row of second passageways 111 parallel to each other.

The contacts 2 comprises a plurality of first contacts 200 received in the first passageways 110 and a plurality of second contacts 201 received in the second passageways 111. The contacts 2 each defines a main body 20, an engaging portion 21 extending horizontally from a top of the main body 20 and a tail portion 22 bent from a bottom of the main body 20. When the contacts 2 are disposed in the passageways 11, the engaging portions 21 of the contacts 2 in different rows extend toward each other.

The three sidewalls 12 each has a pair of datum blocks 13 to position the module 4 therebetween. The pair of datum blocks 13 are positioned on two ends of the sidewall 12 and are discrete with respect to each other. Thus, when the module 4 is assembled into the space of insulative housing 1, module 4 can engage with inner surfaces of the datum blocks 13 to make an accurately connection with the contact 2. Two opposite sidewalls 12 of the sidewalls 12 each further has a recess 15 on an outside surface thereof a limiting portion 16 and a protruding portion 17, the limiting portions 16 extend upwardly from rear ends of the two opposite sidewalls 12, and the protruding portions 17 extend forwardly from the front of the two opposite side wall 12, and each protruding portion 17 is formed with a post 14.

The module 4 comprises a printed circuit board 40 and an accessorial module 41 under the printed circuit board 40, the printed circuit board 40 is retained between the datum blocks 13, the accessorial module 41 protrudes beyond a rear end of the insulative housing 1 and exposes on a rear side of the insulative housing 1.

The cover 3 is made of sheet metal and comprises a flat body plate 31 and two flanges 32 extending downwardly from the body plate 31. The flat body plate 31 has a rectangular hatch 310 on an rear end thereof and an embossment 311 located besides the hatch 310 and pressing upon the printed circuit board 40 of the module 4, the limiting portion 16 of the insulative housing 1 is positioned within the hatch 310. The flange 32 defines a through hole 35 to engage with the post 14 of the insulative housing 1 and has a latching portion 320 to latch with to the recess 15 of the insulative housing 1.

When the electrical connector 100 is assembled, the contacts 2 are received in the insulative housing 1 and the cover 3 is pivotally assembled on the insulative housing 1 by the post 14 of the insulative housing 1 engaging with the through hole 35 of the cover 3, thus the cover 3 can rotate from an opened position to a closed position.

Referring to FIGS. 1-2, showing the opened position and the closed position of the electrical connector 100. First, the cover 3 is opened and the module 4 is disposed therein from the upper of the insulative housing 1. In this position, the printed circuit board 40 of the module 4 is engaged with the inner surfaces of the datum blocks 13 to make an accurately connection with the contacts 2. The accessorial module 41 protrudes out and exposes on the rear end of the insulative housing 1. After the module 4 is disposed into the electrical connector 100, and the cover 3 covers the insulative housing 1 substantially. In this position, a rear edge of the cover 3 extends beyond the sidewalls 12 of the insulative housing 1, the limiting portions 16 of the sidewalls 12 is received in the hatch 310 of the cover 3 and abuts an inner side of the hatch 310. Since the cover 3 is expanded to have a rear edge 314 extend beyond the insulative housing 1, the accessorial module 41 can be pressed by the rear edge 314 of the cover 3, that means the accessorial module 41 can be clamped by the cover 3 and the printed circuit board (not shown). The electrical connector 100 can reliably retain the module 4, especially the accessorial module 41.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. An electrical connector, for conventing electric and optical signal from a module to a printed circuit board, comprising:

an insulative housing comprising plurality of passageways and receiving the module, the insulative housing defining a first opening at a rear end thereof;

a plurality of contacts received in the insulative housing; and a cover being pivotally assembled on a front end of the insulative housing and extending beyond the rear end of the insulative housing, the cover defining a second opening at the back of the first opening and being larger than the first opening.

2. The electrical connector as claimed in claim 1, wherein a part of the module extends beyond the insulative housing and is pressed by a rear edge of the cover.

3. The electrical connector as claimed in claim 2, wherein the cover comprises a body plate and two flanges extending downwardly from the body plate, the body plate has a hatch near a rear side thereof, and an embossment located in front of the hatch and pressing upon the module.

4. The electrical connector as claimed in claim 3, wherein the insulative housing comprises a base and three sidewalls extending upwardly from the base, the sidewalls are formed with a plurality of datum blocks to position the module.

5. The electrical connector as claimed in claim 4, wherein the passageways include a row of first passageways and a row of second passageways parallel to each other, the contacts comprises a plurality of first contacts received in the first passageways and a plurality of second contacts received in the second passageways.

6. The electrical connector as claimed in claim 5, wherein the three sidewalls each has a pair of datum blocks, the datum blocks together formed a space to receive the module therebetween, each pair of datum blocks are positioned on two opposite ends of the sidewall and are discrete with respect to each other.

7. The electrical connector as claimed in claim 6, wherein two opposite sidewall each has a recess on outside surface thereof, a limiting portion extending upwardly from a rear end thereof, and a protruding portion extending forwardly from a front end thereof, the protruding portion is formed with a post.

8. The electrical connector as claimed in claim 7, wherein the flange defines a through hole for the post of the insulative housing passing through to pivotally assemble the cover to the insulative housing and is formed with a latching portion to engage with the recess of the insulative housing.

9. The electrical connector as claimed in claim 1, wherein the contacts each defines a main body, an engaging portion extending horizontally from the main body and a tail portion extending downwardly from the main body, the engaging portion of the contacts in different rows extend toward each other when the contacts are received in the insulative housing.

10. An electrical connector used to transmit electric and optical signal from a module to a circuit substrate, comprising:

an insulative housing receiving the module, comprising a base, three sidewalls extending from the base, and a limiting portion extending from a rear end of the insulative housing, said three sidewalls and limiting portion defining a space for receiving the module, the insulative housing defining a first opening communicated with the space at said rear end;

a plurality of contacts received in the insulative housing; and a cover being pivotally assembled on a front end of the insulative housing, the cover having a body plate with a hatch, the limiting portions of the insulative housing being received in the hatch and abutting an inner side of the hatch.

11. The electrical connector as claimed in claim 10, wherein a rear edge of the cover extends beyond the limiting portion of the insulative housing and the cover defines another space at the back of the first opening, and wherein the module is disposed in said another space and pressed by the rear edge of the cover.

12. The electrical connector as claimed in claim 11, wherein the cover comprises two flanges extending downwardly from the body plate, the body plate has an embossment located in front of the hatch and pressing upon the module.

13. The electrical connector as claimed in claim 12, wherein the three sidewalls are formed with a plurality of datum blocks to position the module.

14. The electrical connector as claimed in claim 13, wherein the three sidewalls each has a pair of datum blocks to position the module in the space, the pair of datum blocks is disposed on two opposite ends of the sidewall and are discrete with respect to each other.

15. The electrical connector as claimed in claim 14, wherein two opposite sidewall of the three sidewalls each has a recess on outside surface thereof and a protruding portion extending forwardly from a front end thereof, the protruding portion is formed with a post.

16. An electrical connector assembly comprising:

an insulative housing defining a base with a pair of side arms rearwardly extending from two opposite ends of said base and cooperating with said base to commonly define a U-shaped configuration in a top view with a receiving space therein;

a recess formed in a top face of said housing and defining generally a square configuration in said top view and laterally restrained by both said base and said side arms;

a plurality of contacts disposed in the base with contacting sections extending upwardly into the recess;

one upward extending protrusion formed at one of distal ends of said side arms for limiting purpose;

a cover have a front end pivotally a front end of the housing and covering said housing; and an optical module including a printed circuit board received in the recess, and an accessorial module occupying said receiving space with thereof a rear portion extending rearwardly beyond the distal ends of the side arms; wherein the cover defining an opening receiving said upward extending protrusion.

17. The electrical connector assembly as claimed in claim 16, wherein an edge of said opening laterally abuts against the upwardly extending protrusion.

18. The electrical connector assembly as claimed in claim 17, wherein said upwardly extending protrusion is located at a corner of said opening.

19. The electrical connector assembly as claimed in claim 17, wherein a top face of said accessorial module is lower than that of the upwardly extending protrusion.

20. The electrical connector assembly as claimed in claim 17, wherein the cover intimately downwardly abuts against both the accessorial module and said printed circuit board.

* * * * *